United States Patent
Fox et al.

(10) Patent No.: US 11,204,955 B2
(45) Date of Patent: Dec. 21, 2021

(54) DIGITAL CONTENT DELIVERY BASED ON PREDICTED EFFECT

(71) Applicant: INTERNATIONAL BUSINESS MACHINES CORPORATION, Armonk, NY (US)

(72) Inventors: Jeremy R. Fox, Georgetown, TX (US); Trudy L. Hewitt, Cary, NC (US); John Rice, Tramore (IE); Liam S. Harpur, Skerries (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 333 days.

(21) Appl. No.: 16/205,870

(22) Filed: Nov. 30, 2018

(65) Prior Publication Data
US 2020/0175056 A1 Jun. 4, 2020

(51) Int. Cl.
G06F 16/20 (2019.01)
G06F 16/435 (2019.01)
G06F 16/438 (2019.01)
A61B 5/00 (2006.01)

(52) U.S. Cl.
CPC .......... *G06F 16/436* (2019.01); *A61B 5/4812* (2013.01); *A61B 5/4815* (2013.01); *A61B 5/4857* (2013.01); *A61B 5/74* (2013.01); *G06F 16/438* (2019.01); *A61B 2503/12* (2013.01)

(58) Field of Classification Search
CPC ... A61B 5/4812; A61B 5/4815; A61B 5/4857; A61B 5/74; G06F 16/436; G06F 16/438
See application file for complete search history.

(56) References Cited

U.S. PATENT DOCUMENTS

| | | | |
|---|---|---|---|
| 9,762,944 B2 | 9/2017 | Sharma | |
| 2005/0119893 A1* | 6/2005 | Shambaugh | H04M 3/51 704/270 |
| 2007/0167689 A1 | 7/2007 | Ramadas et al. | |
| 2009/0279053 A1* | 11/2009 | Sun | G03B 21/00 353/46 |
| 2012/0245924 A1* | 9/2012 | Brun | G06F 40/258 704/9 |
| 2014/0163956 A1* | 6/2014 | Tesch | G06F 40/10 704/9 |
| 2014/0223462 A1 | 8/2014 | Aimone et al. | |
| 2015/0187199 A1* | 7/2015 | Chang | A61B 5/048 340/575 |
| 2015/0297109 A1* | 10/2015 | Garten | A61B 5/0482 600/544 |

(Continued)

FOREIGN PATENT DOCUMENTS

WO 2015006369 A1 1/2015

*Primary Examiner* — Tarek Chbouki
(74) *Attorney, Agent, or Firm* — Cuenot, Forythe & Kim, LLC (57) ABSTRACT

Delivering content based on predicted effect can include analyzing, using computer hardware, digital content before providing the digital content to a device of a user, predicting, using the computer hardware, an effect that the digital content will have on a circadian rhythm of the user, based on the predicted effect, modifying, using the computer hardware, the digital content to generate modified digital content, and providing, using the computer hardware, the modified digital content to the device of the user.

20 Claims, 6 Drawing Sheets

(56) References Cited

U.S. PATENT DOCUMENTS

| | | | |
|---|---|---|---|
| 2016/0019016 A1* | 1/2016 | Koch | G06T 19/006 |
| | | | 345/633 |
| 2016/0294746 A1* | 10/2016 | Boothroyd | H04L 51/38 |
| 2017/0055017 A1 | 2/2017 | Christie et al. | |
| 2017/0136348 A1* | 5/2017 | Hattori | A61B 5/024 |
| 2017/0347906 A1* | 12/2017 | Intrator | A61B 5/6803 |
| 2018/0101524 A1* | 4/2018 | Dunnihoo | G06F 40/14 |
| 2018/0203847 A1* | 7/2018 | Akkiraju | G06F 40/253 |
| 2018/0234739 A1* | 8/2018 | Sreedhara | H04N 21/4884 |
| 2018/0267955 A1* | 9/2018 | Catalano | H04L 51/32 |
| 2018/0279900 A1* | 10/2018 | Moghaddam | A61B 5/0482 |
| 2018/0361109 A1* | 12/2018 | Eng | G09G 5/10 |
| 2019/0254591 A1* | 8/2019 | Garcia Molina | G06F 17/18 |
| 2019/0297035 A1* | 9/2019 | Fox | G06F 16/24575 |
| 2020/0100682 A1* | 4/2020 | Abreu | A61B 5/01 |
| 2020/0167846 A1* | 5/2020 | Aliakseyeu | G06N 5/04 |
| 2020/0178892 A1* | 6/2020 | Maslik | A61B 5/0205 |

* cited by examiner

DIGITAL CONTENT DELIVERY BASED ON PREDICTED EFFECT

BACKGROUND

This disclosure relates to digital content delivery based on predicted effects of the digital content.

Spending large amounts of time in front of computer screens can have detrimental effects on human beings. Long term computer usage, for example, may contribute to Myopia, posture problems, and mental fatigue. Some studies have shown that bright lights from computer and mobile device screens may even alter the natural production of melatonin in the human body. Melatonin is important to the normal sleep-wake cycle in human beings. In addition to screen time in general, the digital content users choose to consume may have a significant impact on the user's well-being. For example, some users may experience a disruption in their sleep-wake cycle.

SUMMARY

In one or more embodiments, a method includes analyzing, using computer hardware, digital content before providing the digital content to a device of a user, predicting, using the computer hardware, an effect that the digital content will have on a circadian rhythm of the user, based on the predicted effect, modifying, using the computer hardware, the digital content to generate modified digital content, and providing, using the computer hardware, the modified digital content to the device of the user.

In one or more embodiments, a system includes a processor configured to initiate executable operations. The executable operations include analyzing digital content before providing the digital content to a device of a user, predicting an effect that the digital content will have on a circadian rhythm of the user, based on the predicted effect, modifying the digital content to generate modified digital content, and providing the modified digital content to the device of the user.

In one or more embodiments, a computer program product includes a computer readable storage medium having program code stored thereon. The program code is executable by a processor to initiate executable operations. The executable operations include analyzing digital content before providing the digital content to a device of a user, predicting an effect that the digital content will have on a circadian rhythm of the user, based on the predicted effect, modifying the digital content to generate modified digital content, and providing the modified digital content to the device of the user.

This Summary section is provided merely to introduce certain concepts and not to identify any key or essential features of the claimed subject matter. Other features of the inventive arrangements will be apparent from the accompanying drawings and from the following detailed description.

BRIEF DESCRIPTION OF THE DRAWINGS

The inventive arrangements are illustrated by way of example in the accompanying drawings. The drawings, however, should not be construed to be limiting of the inventive arrangements to only the particular implementations shown. Various aspects and advantages will become apparent upon review of the following detailed description and upon reference to the drawings.

DETAILED DESCRIPTION

While the disclosure concludes with claims defining novel features, it is believed that the various features described within this disclosure will be better understood from a consideration of the description in conjunction with the drawings. The process(es), machine(s), manufacture(s) and any variations thereof described herein are provided for purposes of illustration. Specific structural and functional details described within this disclosure are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to digital content delivery based on predicted effect on a user. In accordance with the inventive arrangements described within this disclosure, a system is capable of managing the output and/or delivery of digital content to a user (e.g., a device of the user). The system is capable of managing the delivery of digital content based on the user's unique, personal historical reaction to specific digital content, based on crowd sourced data, or a combination of both in order to achieve a better outcome for the user's wellbeing.

In one or more embodiments, the system is capable of monitoring a user's circadian rhythm(s) using various sensors capable of conveying data. The sensor data may include biometric data for the user. The system is capable of using the sensor data to monitor a circadian rhythm of the user such as the user's sleep cycle. The system is capable of correlating the user's sleep cycle over time with consumption of digital content and, therefore, device usage. Device usage and/or content consumption prior to sleep, for example, may induce particular emotional states or otherwise be disruptive to the circadian rhythm of the user.

By monitoring the user's circadian rhythm(s) over time and device usage and/or consumption of digital content, the system is capable of predicting whether using a device and/or consuming digital content via a device will have an effect on the user. The effect on the user may be a disruption in the circadian rhythm of the user. Based on the prediction, the system is capable of managing or controlling aspects of the delivery of digital content to the user. For example, the system is capable of predicting the effect of certain digital content on the sleep cycle of the user based on historical data that correlates the user's digital content consumption, crowd sourced data, or both with the user's sleep cycle.

In particular embodiments, the system is capable of modifying the digital content that is delivered to the user so that any disruptive effect on the user's circadian rhythms that may have been caused by consumption of the digital content in original form is reduced or eliminated. For example, the system is capable of modifying the digital content by toning down aspects of the digital content. The system, for example, may replace words within text with less intense words that have the same or similar meaning as the words being replaced. The system may reduce color intensity of images and/or video to be provided to the user. The system may replace particular scenes in a movie and/or video with alternative scenes that are less graphic or have less intense action.

Further aspects of the embodiments described within this disclosure are described in greater detail with reference to the figures below. For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features.

It is understood in advance that although this disclosure includes a detailed description on cloud computing, implementations of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1:
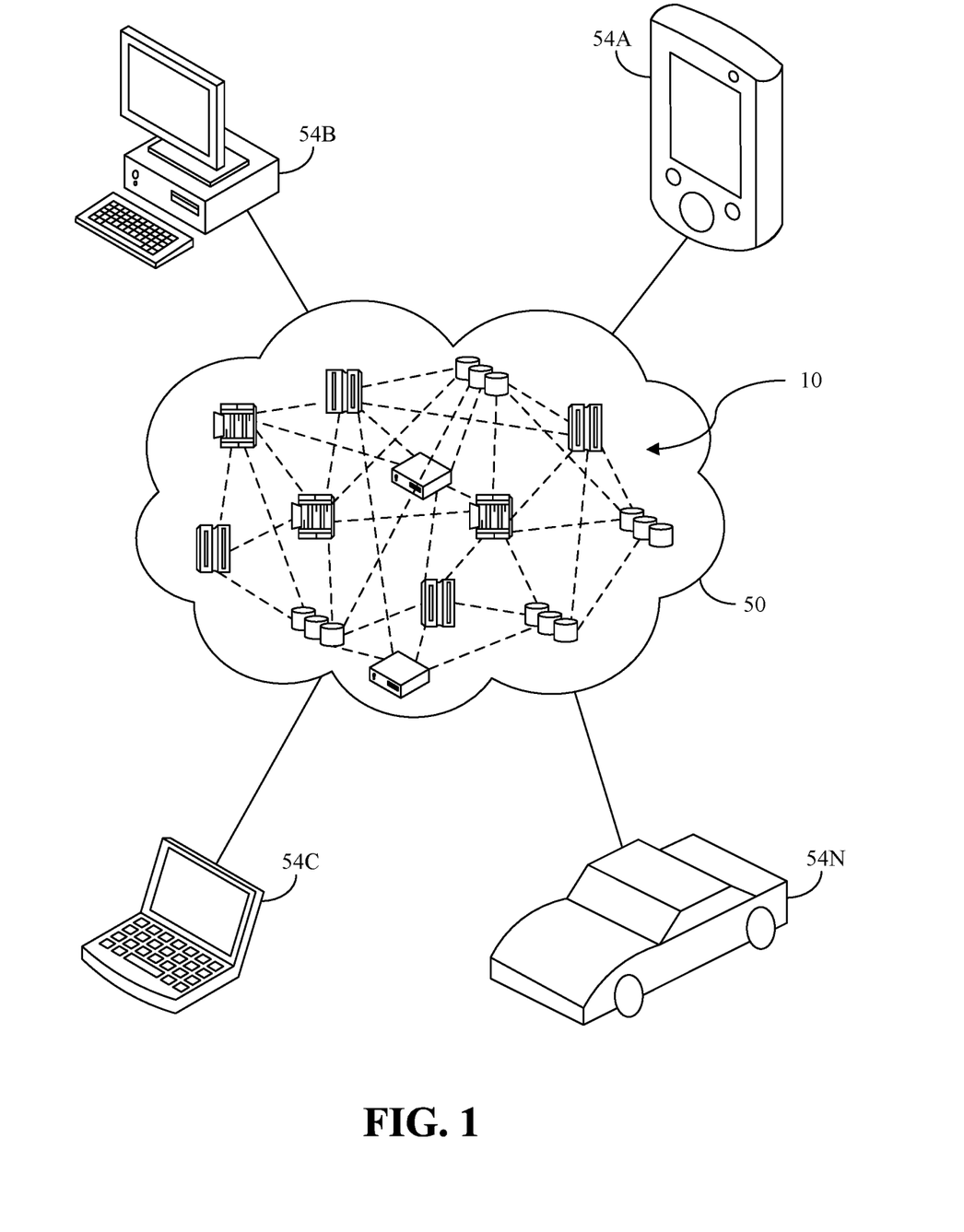
FIG. 1 depicts a cloud computing environment according to an embodiment of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
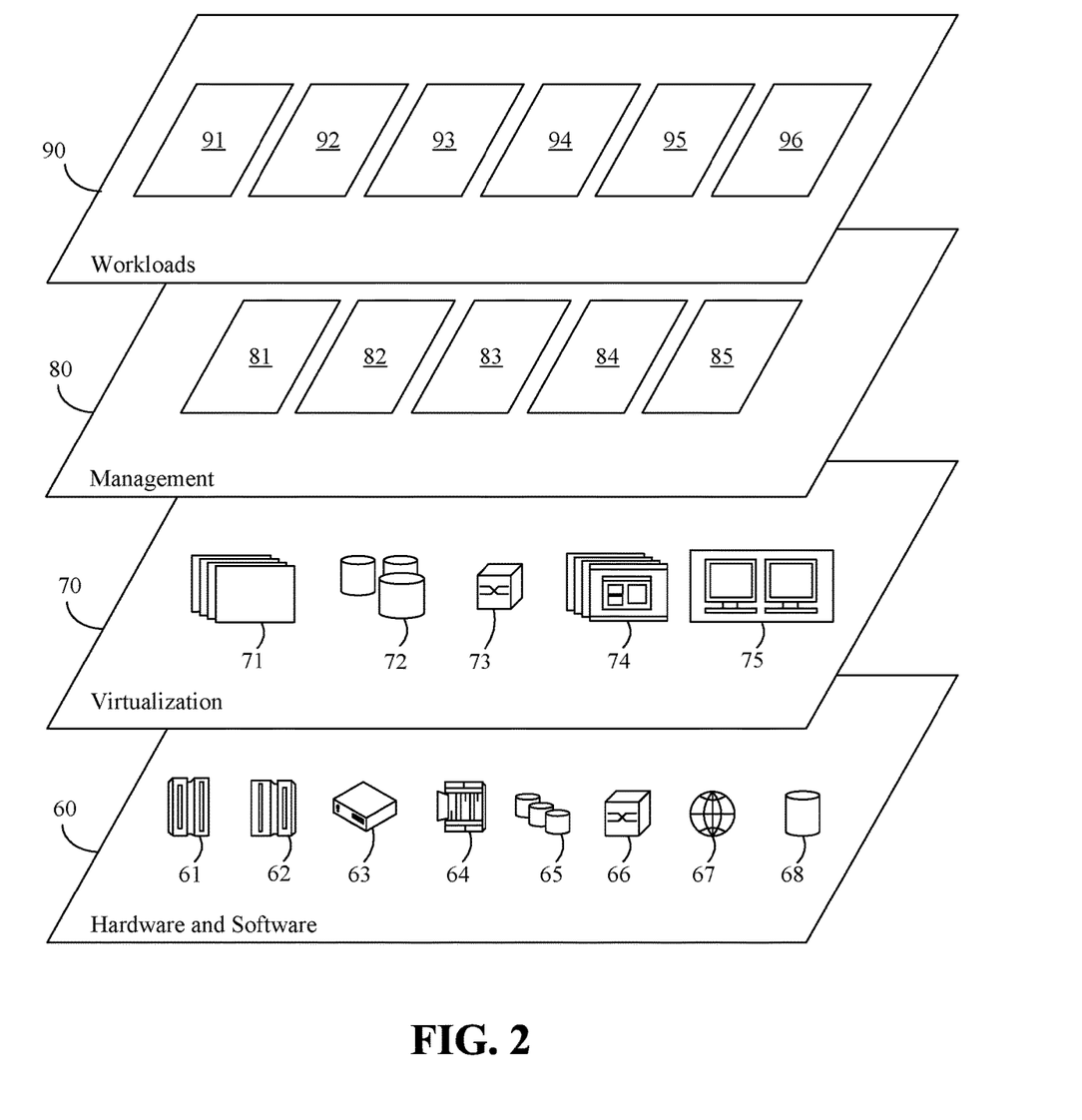
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA. Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and content delivery system (system) 96.

System 96 is capable of controlling the delivery of digital content to a user device. For example, system 96 is capable of analyzing, using computer hardware, digital content before providing the digital content to a user through a user device and predicting, using the computer hardware, an effect that the digital content will have on a circadian rhythm of the user. In many cases, users choose to consume digital content at night and/or prior to sleep. The digital content may be electronic books, videos, movies, television shows, or the like. In some cases, the digital content may bother the user or invoke an emotional state that is not conducive to the user's circadian rhythms. As discussed, an example of a circadian rhythm is the sleep cycle of the user.

System 96 is capable of comparing digital content to be delivered to the user's device at particular times or during particular time periods with historical data for the user and/or other users. The historical data correlates circadian rhythms of the user and/or other users with prior consumed digital content and times of delivery of the prior consumed digital content for the user and/or other users. Based on the predicted effect the digital content will have on the user, system 96 is capable of modifying the digital content prior to delivery to the user's device to generate modified digital content. For example, system 96 is capable of modifying the digital content by toning down the digital content to generate the modified digital content. In another example, system 96 modifies the digital content by time shifting the digital content prior to delivery. System 96 is capable of delivering the modified digital content to the user's device. The modified digital content may be rendered by the user device.

By providing the user with the modified digital content, system 96 increases the likelihood that the user's sleep cycle will not be degraded. System 96 is able to manage delivery of digital content to the user to improve the user's sleep cycle prior to going to sleep, rather than inform the user after the fact, e.g., the next morning after waking, that the digital content the user consumed the prior evening may have been disruptive to the user's sleep cycle.

Figure 3:
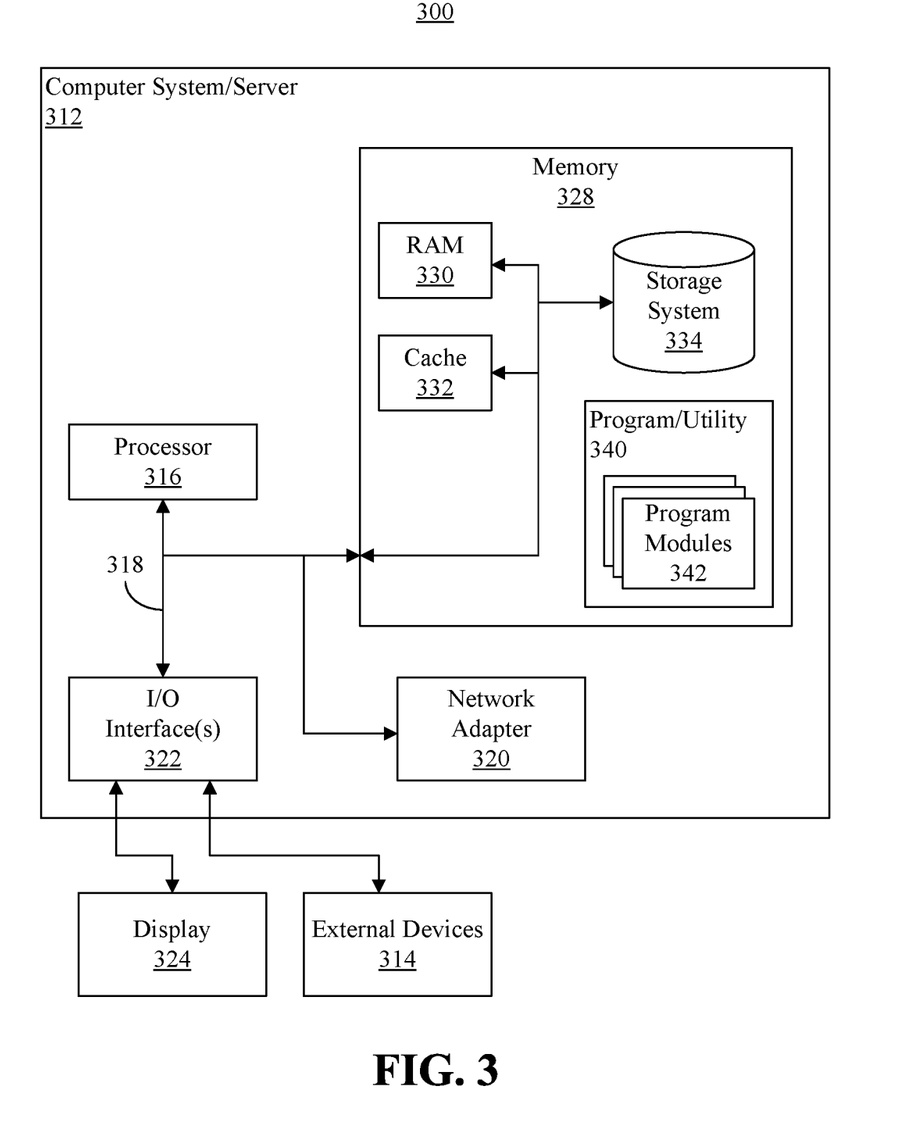
FIG. 3 depicts a cloud computing node according to an embodiment of the present invention.

FIG. 3 illustrates a schematic of an example cloud computing node. Cloud computing node 300 is only one example of a suitable cloud computing node and is not intended to suggest any limitation as to the scope of use or functionality of embodiments of the invention described herein. Regardless, cloud computing node 300 is capable of being implemented and/or performing any of the functionality set forth hereinabove.

Cloud computing node 300 includes a computer system/server 312, which is operational with numerous other general purpose or special purpose computing system environments or configurations. Examples of well-known computing systems, environments, and/or configurations that may be suitable for use with computer system/server 312 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 312 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 312 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 312 in cloud computing node 300 is shown in the form of a general-purpose computing device. The components of computer system/server 312 may include, but are not limited to, one or more processors 316, a memory 328, and a bus 318 that couples various system components including memory 328 to processor 316.

Bus 318 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, and PCI Express (PCIe) bus.

Computer system/server 312 typically includes a variety of computer system readable media. Such media may be any available media that is accessible by computer system/server 312, and it includes both volatile and non-volatile media, removable and non-removable media.

Memory 328 can include computer system readable media in the form of volatile memory, such as random access memory (RAM) 330 and/or cache memory 332. Computer system/server 312 may further include other removable/non-removable, volatile/non-volatile computer system storage media. By way of example, storage system 334 can be provided for reading from and writing to a non-removable, non-volatile magnetic media and/or solid state drive(s) (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 318 by one or more data media interfaces. As will be further depicted and described below, memory 328 may include at least one program product having a set (e.g., at least one) of program modules that are configured to carry out the functions of embodiments of the invention.

Program/utility 340, having a set (at least one) of program modules 342, may be stored in memory 328 by way of example, and not limitation, as well as an operating system, one or more application programs, other program modules, and program data. Each of the operating system, one or more application programs, other program modules, and program data or some combination thereof, may include an implementation of a networking environment. Program modules 342 generally carry out the functions and/or methodologies of embodiments of the invention as described herein.

For example, one or more of the program modules may include system 96 or portions thereof. Program/utility 340 is executable by processor 316. Program/utility 340 and any data items used, generated, and/or operated upon by node 300 are functional data structures that impart functionality when employed by node 300. As defined within this disclosure, a "data structure" is a physical implementation of a data model's organization of data within a physical memory. As such, a data structure is formed of specific electrical or magnetic structural elements in a memory. A data structure imposes physical organization on the data stored in the memory as used by an application program executed using a processor.

Computer system/server 312 may also communicate with one or more external devices 314 such as a keyboard, a pointing device, a display 324, etc.; one or more devices that enable a user to interact with computer system/server 312; and/or any devices (e.g., network card, modem, etc.) that enable computer system/server 312 to communicate with one or more other computing devices. Such communication can occur via Input/Output (I/O) interfaces 322. Still yet, computer system/server 312 can communicate with one or more networks such as a local area network (LAN), a general wide area network (WAN), and/or a public network (e.g., the Internet) via network adapter 320. As depicted, network adapter 320 communicates with the other components of computer system/server 312 via bus 318. It should be understood that although not shown, other hardware and/or software components could be used in conjunction with computer system/server 312. Examples, include, but are not limited to: microcode, device drivers, redundant processing units, external disk drive arrays, RAID systems, tape drives, and data archival storage systems, etc.

While node 300 is used to illustrate an example of a cloud computing node, it should be appreciated that a computer system using an architecture the same as or similar to that shown in FIG. 3 may be used in a non-cloud computing implementation to perform the various operations described herein. In this regard, the example embodiments described herein are not intended to be limited to a cloud computing environment. Node 300 is an example of a data processing system. As defined herein, the term "data processing system" means one or more hardware systems configured to process data, each hardware system including at least one processor programmed to initiate executable operations and memory.

Node 300 is also an example of a server. As defined herein, the term "server" means a data processing system configured to share services with one or more other data processing systems. For example, the server may be an e-mail server configured to share services with one or more client devices (e.g., email client devices). As defined herein, the term "client device" means a data processing system that requests shared services from a server, and with which a user directly interacts. Examples of a client device include, but are not limited to, a workstation, a desktop computer, a computer terminal, a mobile computer, a laptop computer, a netbook computer, a tablet computer, a smart phone, a personal digital assistant, a smart watch, smart glasses, a gaming device, a set-top box, a smart television and the like. In one or more embodiments, the various user devices described herein may be client devices. Network infrastructure, such as routers, firewalls, switches, access points and the like, are not client devices as the term "client device" is defined herein.

Figure 4:
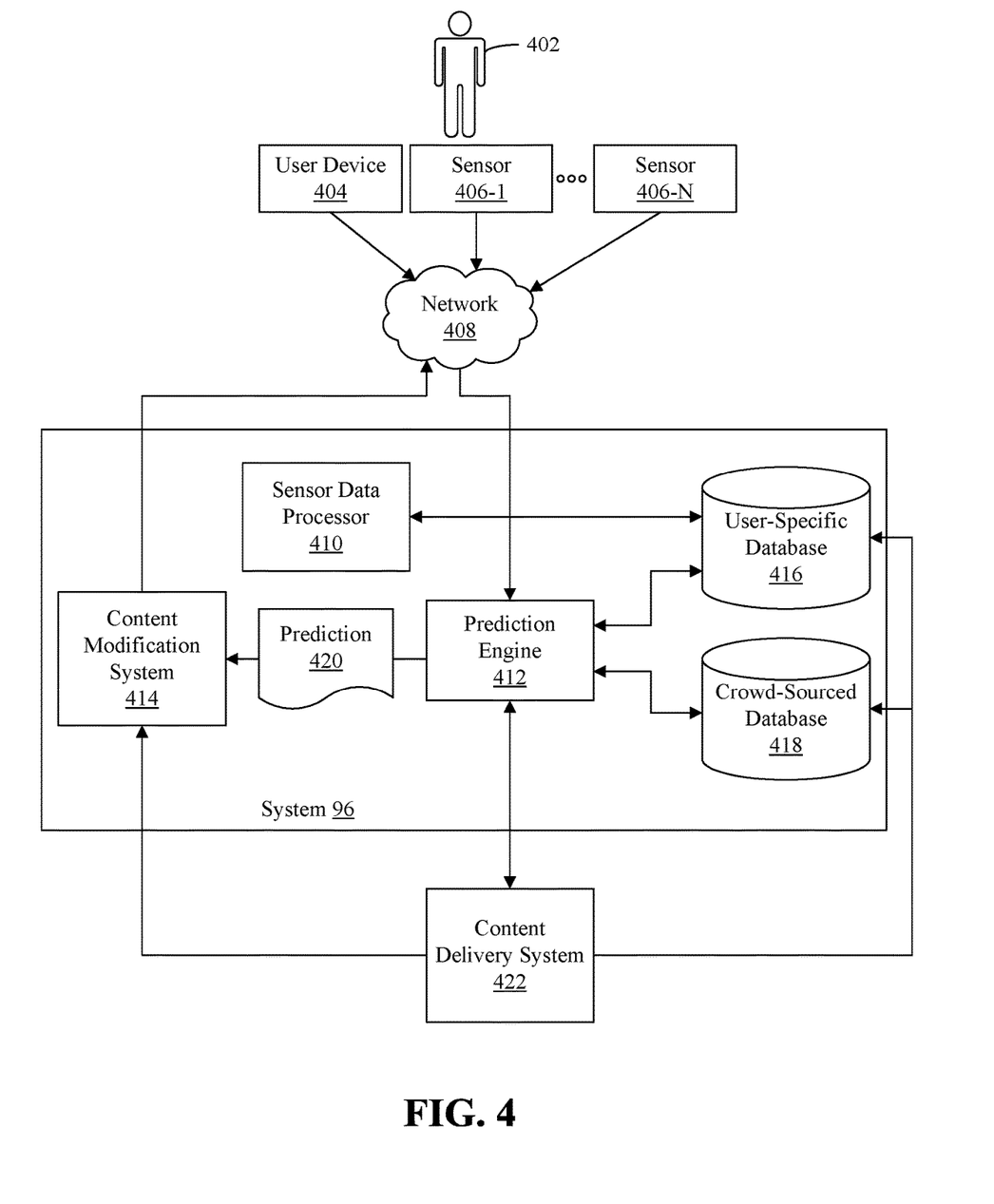
FIG. 4 depicts a computing environment for use in predicting the effect that digital content will have on a user according to an embodiment of the present invention.

FIG. 4 depicts an example computing environment 400 for use in predicting the effect that digital content will have on a user according to an embodiment of the present invention. In the example of FIG. 4, a user 402 has a user device 404 through which user 402 is able to consume digital content. Examples of digital content can include, but are not limited to, video such as movies, television shows, audio such as music and/or songs, podcasts, audiobooks, online video game, Websites, and/or other textual information such as online articles, documents, and electronic books. Certain types of the digital content such as audio and/or video may be streamed.

User device 404 is capable of rendering, or playing, the digital content for the user. For example, user device 404 may be a computer, a tablet computer, a mobile phone such as a smart phone, a gaming console, an entertainment console (e.g., a television provider console unit for cable or other technology), an e-reader, a smart television such as an internet enabled television, internet enabled speaker, a smart appliance, a smart watch, or the like. In the example of FIG.

4, a single user device 404 is illustrated. It should be appreciated, however, that user 402 may be associated with and/or be able to consume digital content through a plurality of different user devices (e.g., a mobile phone, a television console, and a smart television) not shown in FIG. 4.

In the example of FIG. 4, user 402 may be monitored by one or more sensors 406. Sensors 406 may include, but are not limited to, visual sensors such as a camera, audio sensors such as microphones, accelerometers, gyroscopes, location sensors such as global positioning system (GPS) receivers, and the like. One or more of sensors 406 may be standalone sensors. In particular embodiments, one or more or all of the sensors 406 are incorporated into user device 404 (and/or other user devices). For example, a laptop computer, a tablet computer, and a mobile phone are typically equipped with a microphone and a forward-facing camera to observe or capture user reactions. Mobile phones, smart watches, and/or tablet computers are often equipped with accelerometers and gyroscopes. Other examples of sensors may include, but are not limited to, step counters, exercise and/or jogging equipment capable of measuring heartrate, respiratory rate, steps taken, distance traveled, and/or other biometric data, and/or Internet of Things (IoT) devices.

User device 404 and sensors 406 are communicatively linked to system 96 through a network 408. Network 408 is the medium used to provide communication links between various devices and data processing systems connected together within network computing system 400. Network 408 may include connections, such as wired communication links, wireless communication links, or fiber optic cables. Network 408 may be implemented as, or include, one or more or any combination of different communication technologies such as a Wide Area Network (WAN), a Local Area Network (LAN), a wireless network (e.g., a wireless WAN and/or a wireless LAN), a mobile or cellular network, a Virtual Private Network (VPN), the Internet, the Public Switched Telephone Network (PSTN), and so forth.

In the example of FIG. 4, system 96 may be implemented in one or more cloud computing nodes as described herein and/or other data processing system having an architecture the same as or similar to that illustrated in FIG. 3. As pictured, system 96 includes a sensor data processor 410, a prediction engine 412, and a content modification system 414. System 96 may also include a variety of different data storage devices for storing various types of data. For example, system 96 may include a user-specific database 416 and/or a crowd-sourced database 418. It should be appreciated that the types of data described within this disclosure may be stored in any of a variety of different types of data structures and that use of a database is for purposes of illustration and not limitation.

In one or more embodiments, content delivery system 422 is capable of interfacing with system 96 to store records of digital content provided to user device 404 (or another device of user 402) from content delivery system 422 (or other content delivery systems) in user-specific database 416. For example, content delivery system 422 may interact with system 96 through an application programming interface (API) to store records of digital content delivered to user device 404. As such, user-specific database 416 may include a history of digital content consumed by user 402 over a period of time such as days, weeks, months, or the like. The records stored in user-specific database 416 may indicate the particular item of digital content provided, metadata describing the item of digital content, and the time that, or time span over which, the item of digital content was provided to user device 404. Depending on the type of digital content delivered by content delivery system 422, the metadata stored within the record in user-specific database 416 may vary.

For example, the metadata for an item of digital content may specify a rating (e.g., G, R, PG, PG-13, etc.) and/or type of material included in the digital content (e.g., violence, adult content, strong language, etc.). Other examples of metadata that may be included in the record for an item of digital content include genre, author, writer, other bibliographic data for the digital content, and/or actor(s) in the digital content if applicable. The digital content may be tagged and/or annotated with any of a variety of descriptive tags that may be stored as part of the metadata within the record stored in user-specific database 416.

System 96 is also capable of receiving sensor data generated by one or more or all of sensors 406. In one or more embodiments, the sensor data may be raw sensor data generated by the respective sensors 406. In one or more other embodiments, the sensor data may be processed by a device that includes one or more sensors 406 to output enhanced sensor data. For example, a smart phone or other device that includes one or more sensors 406 and processing capability is capable of processing the raw sensor data to output information about the circadian rhythms of user 402 directly to system 96. As an illustrative and nonlimiting example, a user device equipped with sensors is capable of outputting sleep cycle data directly to system 96. In cases where system 96 receives raw sensor data, system 96 is capable of generating sleep cycle data from the raw sensor data. In any case, the sensor data may be provided to sensor data processor 410 and/or to prediction engine 412.

In one or more embodiments, sensor data processor 410 is capable of processing the received sensor data to determine one or more circadian rhythms of user 402 (e.g., if not already specified by the sensor data directly). As defined within this disclosure, a "circadian rhythm" is any biological process within a user that displays an endogenous, entrainable oscillation of about 24 hours. The sleep cycle of user 402 is an example of a circadian rhythm of user 402. In determining the sleep cycle of user 402, sensor data processor 410 is capable of determining attributes of the sleep cycle of user 402 such as length of sleep, amount of sleep, whether rapid eye movement (REM) sleep was achieved, and/or amount of REM sleep obtained on a daily or nightly basis. As noted, in some cases, a user device may directly provide sleep cycle data to sensor data processor 410. In the example of FIG. 4, sensor data processor 410 is capable of storing circadian rhythms such as sleep cycle data, whether calculated by system 96 or received from a user device, for user 402 within user-specific database 416. In particular embodiments, sensor data processor 410 may also store the received sensor data directly in user-specific database 416. In any case, sensor data for the user may be stored over days, weeks, months, or the like for the same time that the consumption of digital media by user 402 is recorded.

In one or more embodiments, sensor data processor 410 is capable of analyzing other sensor data such as received images of the user, received audio of the user, accelerometer data for the user, and/or biometric data for the user while the user is consuming digital content. As such, sensor data processor 410 is capable of determining the reaction of the user to particular digital content. For example, sensor data processor 410 is capable of determining an emotional reaction of user 402 to digital content via image processing to recognize facial feature recognition, perform voice analysis to recognize various tones and/or emotions, perform Natural Language Processing (e.g., of speech recognized text), and the like. The reaction of user 402 to digital content may be stored in user-specific database 416 within a record that may be associated with the record for the item of digital content being consumed while the sensor data is generated and/or analyzed.

Natural Language Processing (NLP) is a field of computer science, artificial intelligence and computational linguistics which implements computer processes to facilitate interactions between computer systems and human (natural) languages. NLP enables computers to derive computer-understandable meaning from natural language input. The International Organization for Standardization (ISO) publishes standards for NLP, one such standard being ISO/TC37/SC4. As part of NLP, semantic analysis may be performed. Semantic analysis may follow parsing and involve extraction of context-independent aspects of a sentence's meaning, including entities, named entities, the semantic roles of entities mentioned in the sentence, semantic analysis, tone analysis (e.g., for determining emotive content), and quantification information, such as cardinality, iteration, and dependency.

In one or more embodiments, prediction engine 412 is capable of analyzing sensor data (e.g., sleep data) for user 402 and records of digital content consumed by user 402. Prediction engine 412 is capable of correlating items of digital content consumed by user 402 within a period of time preceding sleep or attempting to sleep (e.g., preparing for bed) with the ensuing sleep cycle of user 402. Prediction 412 is capable of quantifying the quality of a user's sleep cycle in terms of length of sleep, amount of sleep, whether rapid eye movement (REM) sleep was achieved, amount of REM sleep obtained, and/or any combination thereof (e.g., a function thereof) for a given night or sleep session. In particular embodiments, system 96 is capable of determining a sleep quality baseline by determining an average measure of sleep quality of user 402 over time. Other statistical techniques may also be used to determine a sleep quality baseline for user 402.

For purposes of illustration, consider an example where user 402 uses a smart phone for approximately 45 minutes and then discontinues use of the smart phone for approximately 10 minutes prior to falling asleep. User 402 may be reading graphic content and/or viewing graphic images during the 45 minute time span of smart phone use. In that case, system 96 is capable of monitoring the sleep cycle of user 402 to determine the quality of sleep obtained. System 96 is capable of learning whether use of the smart phone and/or the content consumed by user 402 prior to going to sleep had a detrimental effect on the quality of sleep achieved by user 402. For example, system 96 may detect that the user was restless and had a lower quality of sleep compared to the sleep quality baseline.

In another example, system 96 may detect that in response to particular digital content, e.g., a horror movie, user 402 required extra time, e.g., an extra hour, to fall asleep. In that case, system 96 is capable of learning the correlation between the digital content consumed and the delay in falling asleep.

In another example, system 96 may determine, from sensor data from user 402, e.g., heartrate, respiratory rate, accelerometer data indicating movement, or the like, that user 402 has entered an agitated state or an emotional state that is not conducive to quality sleep while consuming particular digital content.

In one or more other embodiments, prediction engine 412 is capable of performing the same or similar functions with respect to one or more other users. As such, prediction engine 412 may generate same or similar data and store such data within crowd-source database 418.

Having collected sensor data and/or digital media consumption data, prediction engine 412 may be trained using the collected data. In particular embodiments, prediction engine 412 is implemented as a trained neural network. Prediction engine 412 may be trained to a point where the weights of the neural network have converged or substantially converged to generate a prediction of whether digital content to be consumed by a user is likely to disrupt a circadian rhythm of user 402. Prediction engine 412 may be trained using user-specific database 416, using crowd-source database 418, or a combination thereof. In particular, a training process has determined a set of weights for the nodes of the neural network that provides the neural network with the desired input-output relationship to generate prediction values over time based on the inputs provided. To this end, a learning process may be used to adjust the weights of the neural network to change the input-output relationship so that an input-output accuracy cost function is optimized. Thus, the goal of a training process is to change the input-output relationship of prediction engine 412.

In the example of FIG. 4, the training of prediction engine 412 may be performed so that given an item of digital content (e.g., a description of such an item which may include metadata for the item) and a time or window of time that the digital content is to be consumed by user 402, prediction engine 412 is capable of generating a prediction 420 of whether the item of digital content will disrupt a circadian rhythm of user 402, e.g., result in degraded quality of sleep. The prediction may be expressed as a value between 0 and 1, for example. Further, prediction 420 may be a user-specific prediction, a crowd-sourced-based prediction, include both a user-specific prediction and a crowd-sourced prediction, or be a combination of the two types of predictions.

With prediction engine 412 trained, prediction engine 412 may begin operating in a real time and/or near real time mode of operation. In this mode of operation, prediction engine 412 may be informed of particular digital content requested by user 402 and/or to be provided to user 402 by content delivery system 422. An example of a request may be user 402 streaming content and a new show or movie starting automatically through an online content provider after the completion of a prior item of digital content, an explicit request for content, or the like.

In one or more embodiments, prediction engine 412 is notified of content to be provided to user 402 prior to content delivery system 422 actually providing or delivering the digital content to a device of user 402. Prediction engine 412 is capable of analyzing the digital content to be delivered to the user prior to delivery to user 402 by comparing the digital content to be delivered with prior consumed digital content that was determined to have been correlated with a disruption in a circadian rhythm of user 402. For purposes of discussion, content to be delivered to user 402 that is undergoing analysis to generate a prediction is referred to as "selected digital content."

Prediction engine 412 is capable of outputting a prediction 420 specifying a likelihood of whether the digital content will result in a disruption in a circadian rhythm of user 402 such as low-quality sleep. In the example of FIG. 4, prediction engine 412 provides prediction 420 to content modification system 414. Based on prediction 420, content modification system 414 is capable of modifying the digital content to be delivered to user 402 prior to delivery to user device 404. For example, content modification system 414 is capable of intercepting the selected digital content delivered by content delivery system 422 and applying one or more modifications to the selected digital content thereby resulting in modified digital content. The modified digital content generated by content modification system 414 is modified in a manner that reduces the likelihood that the selected digital content, as modified by content modification system 414, will cause low or reduced quality sleep for user 402 when consumed within a predetermined amount of time prior to the user going to bed or to sleep.

In one or more embodiments, prediction engine 412 is also capable of providing a notification and/or prediction 420 to a device of user 402. For example, prediction engine 412 is capable of sending a message to user device 404 indicating that the selected digital content may cause user 402 to have low quality sleep and/or cause a disruption in a circadian rhythm of user 402. In that case, prediction engine 412 may await a response from user 402 approving modification of the selected digital content prior to initiating any modification of the selected digital content. For example, prediction engine 412 may instruct content modification system 414 to modify the selected digital content only in response to obtaining permission from user 402 to do so.

As discussed, prediction engine 412 is capable of intervening to initiate modification of selected digital content based on analysis of user-specific data. In one or more other embodiments, prediction engine 412 is capable of performing a similar analysis and intervening to initiate modification of selected digital content to be delivered to user 402 based upon an analysis of crowd-sourced data stored in crowd-source database 418. For example, in response to determining that selected digital content is the same or similar to digital content found to have caused low quality sleep and/or a disruption in a circadian rhythm of one or more other users, prediction engine 412 may predict that the selected digital content will likely have the same effect on user 402. In response thereto, prediction engine 412 may initiate modification of the selected digital content and/or provide a notification to user 402 as described above.

In one or more embodiments, when using crowd sourced data, prediction engine 412 is capable of using only crowd sourced data for users with similar attributes to those of user 402. For example, prediction engine 412 may use crowd sourced data corresponding to users of a same age as user 402, same gender, same level of education, demographics, etc. when generating a prediction for user 402 using crowd source database 418.

In one or more other embodiments, the type of digital content that is modified need not be graphic or negative digital content. For example, the content may be music of a particular genre or having a particular tempo. In that case, system 96 is capable of modifying the digital content by adjusting the tempo of the music, e.g., by slowing the tempo of the music. In still another example, system 96 may modify the digital content by reducing the volume of the music.

Figure 5:
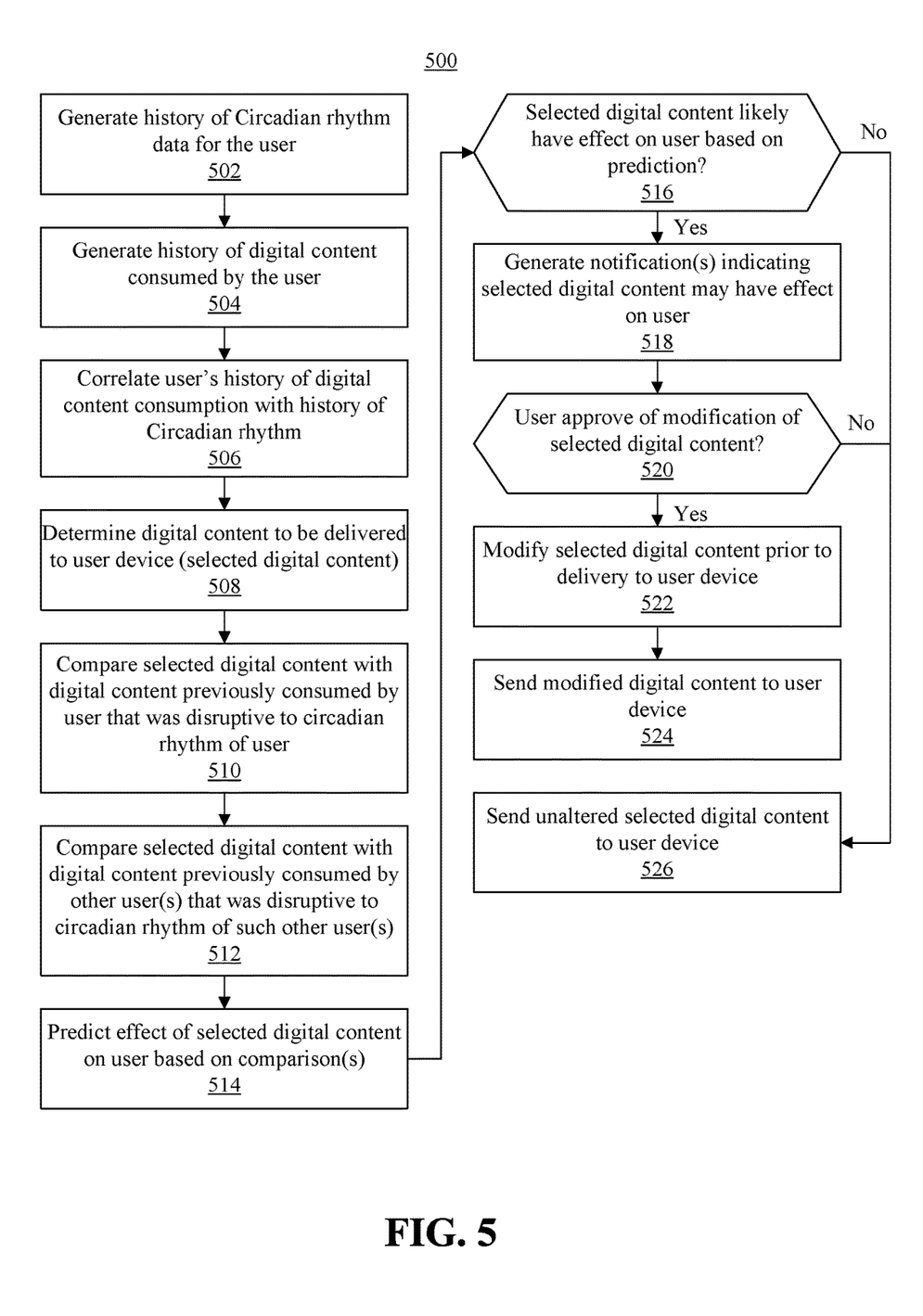
FIG. 5 depicts a method of delivering digital content to a user device based on predicted effect of the digital content on the user according to an embodiment of the present invention.

FIG. 5 depicts a method 500 of delivering digital content to a user device based on predicted effect of the digital content on the user according to an embodiment of the present invention. Method 500 may be implemented by a system the same as or similar to the system described in connection with FIGS. 1-4.

In block 502, the system is capable of generating a history of circadian rhythm data for a user. As discussed, the circadian rhythm data may include sleep data. The circadian rhythm data may be collected over a period of days, weeks, months, etc. Further, as discussed, the circadian rhythm data may be determined based on sensor data collected from the user. The system may use the historical circadian rhythm to determine a baseline for the user, e.g., a baseline quality of sleep.

In one or more embodiments, as part of generating historical circadian rhythm data, the system is capable of storing the user's reaction to consuming digital content at the time of consumption. For example, the system is capable of detecting the emotion on the user's face while viewing a video, reading an electronic book, etc. using visual sensor data and image processing. As an illustrative and nonlimiting example, the system is capable of detecting facial expressions such as where the expression on the user's face turns from one of normal or joy to discussed.

In block 504, the system is capable of generating a history of digital content consumed by the user. In block 506, the system is capable of correlating the historical digital content consumption of the user with the historical circadian rhythm data of the user to determine types of content that cause a disruption in a circadian rhythm of the user. An example of a disruption in a circadian rhythm of the user is low quality sleep. In one or more embodiments, the system is trained using the historical data collected. As discussed, the historical circadian rhythm data may also include reactions of the user detected as the user is consuming items of digital content.

In block 508, the system is capable of determining digital content to be delivered to the user's device (referred to in the context of FIG. 5 as the "selected digital content"). In one or more embodiments, the system is notified of selected digital content by a content delivery system and or by the user's device. In one example, the user's device may submit a request for content through system 96.

In particular embodiments, the system is capable of analyzing selected digital content only during particular times. For example, the system may analyze selected digital content to provide a prediction only during a predetermined amount of time preceding a time that the user begins preparing for sleep and/or goes to sleep. As discussed, the time that the user goes to sleep or begins preparing for sleep may be determined from a historical analysis of the user's sleep cycle and/or from a device of the user that may be configured to indicate to the user when to begin preparing for sleep.

In block 510, the system is capable of comparing the selected digital content with digital content previously consumed by the user that was found to have caused a disruption in a circadian rhythm of the user. In block 512, the system is capable of optionally comparing the selected digital content with digital content previously consumed by one or more other users that was disruptive to a circadian rhythm of such other users. In particular embodiments, blocks 510 and/or 512 may be performed by processing a description of the selected digital content through a trained neural network.

In block 514, the system is capable of predicting an effect of the selected digital content on the user based on the comparison or comparisons performed. For example, the neural network is capable of generating a prediction for the selected digital content. In block 516, the system determines whether the selected digital content will likely have an effect on the user based on the prediction generated in block 514. In response to determining that the selected digital content will likely have an effect on the user based on the prediction, method 500 continues to block 518. In response to determining that the selected digital content will not likely have an effect on the user based on the prediction, method 500 continues to block 526.

For example, the selected digital content may be an action-packed movie or a horror electronic book. The system is capable of generating a prediction indicating that the selected digital content is likely to cause a disruption in his circadian rhythm of the user. System is capable of generating a prediction that takes the user's personal reactions, feelings, and/or fears (e.g., of dogs, clowns, etc.) into account. As discussed, the system may also use crowd-sourcing to generate predictions.

In block 518, the system optionally generates a notification and provides the notification to a device of the user. The notification may indicate that the requested content may have a detrimental effect on the user. The notification may also include a prompt or query asking whether the user would like the system to deliver the selected digital content in a modified form so as to reduce the likelihood that the requested digital content, as modified, will have an effect on the user.

In block 520, the system determines whether the user approves of modification of the selected digital content. In response to determining that the user has indicated approval for modification of the selected digital content, method 500 continues to block 522. In response to determining that the user has indicated disapproval of modification of the selected digital content, method 500 continues to block 526.

In block 522, the system is capable of modifying the selected digital content prior to delivery to the user device. For example, the system is capable of producing a modified version of the selected digital content based on one or more user specified requirements, one or more user preferences, an estimation of the user's emotional state (e.g., based on real time and/or near real time sensor data), or other measured data which may include biometric data. Taking the example of a horror book, for example, the system is capable of replacing graphic language with less edgy or tone down language with the same or similar meaning. As an illustrative and nonlimiting example, the system may replace language referring to specific violent acts such as "cut and bloodied" with toned down replacement language such as "hurt". In block 524, the system is capable of sending the modified digital content to the user device.

In another example, the system is capable of simplifying the selected digital content thereby making the selected digital content easier for the user to consume. For example, at times where the system detects that the user is likely to be tired such as prior to sleep, the system may modify the selected digital content by replacing longer and/or more difficult words in text with replacement text that is easier for the user to understand without negatively impacting the sentiment of the text.

In another example, the system may notify a user the based on prior consumption of similar digital content the user may require a longer time to disengage from the digital content prior to going to sleep.

In block 526, the system is capable of sending the unaltered, or unmodified, selected digital content to the user device.

While the system is capable of analyzing digital content prior to delivery to a user and possibly modifying such digital content prior to delivery, in one or more embodiments, the system is capable of initiating modification of the digital content after the start of delivery. For example, the system is capable of monitoring a user's reaction to content in real time and/or near real time using the sensor data described. In response to determining that the user's emotional state is being altered during consumption of the digital content in a manner indicative of a likely disruption to the user's sleep cycle, the system may begin modifying the digital content being delivered to the user.

In one or more other embodiments, the system is capable of using the sensor data collected from the user while the user is consuming the digital content to determine a degree to which the digital content should be toned down. For example, in cases where the system is able to choose among multiple different options for toning down content, wherein each different option has a different degree of edginess (e.g., choosing between multiple different scenes or multiple different text replacements of varying edginess), the system may choose increasingly toned down options in response to detecting that the user is still becoming agitated over the modified digital content. In this manner, the system is capable of controlling the delivery of the digital content to the user based on real time and/or near real time reactions of the user to the digital content being consumed.

Figure 6:
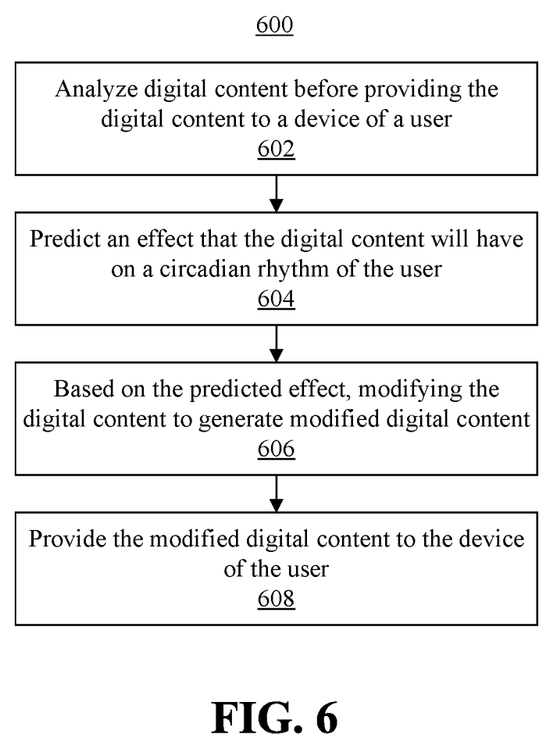
FIG. 6 depicts a method of delivering digital content to a user device based on predicted effect of the digital content on the user according to another embodiment of the present invention.

FIG. 6 illustrates a method 600 of delivering digital content to a user device based on predicted effect of the digital content on the user according to another embodiment of the present invention. Method 600 may be performed by system the same as or similar to the system described in connection with FIG. 1-4.

In block 602, the system is capable of analyzing digital content before providing the digital content to a device of a user. In block 604, the system is capable of predicting an effect that the digital content will have on a circadian rhythm of the user. The system is capable of generating the prediction by, at least in part, comparing the digital content and a time that the digital content is to be presented to the user with historical data for the user that correlates the circadian rhythm of the user with prior consumed digital content and times of delivery of the prior consumed digital content. In block 606, based on the predicted effect, the system is capable of modifying the digital content to generate modified digital content. The system is capable of toning down the digital content. For example, the wherein the modifying the digital content includes replacing a portion of the digital content with an alternative portion of the digital content or slowing tempo of the digital content. In block 608, the system is capable of providing the modified digital content to a device of the user.

Within this disclosure, particular embodiments are described relating to sleep cycle of a user. Inventive arrangements may also be applied to other aspects of circadian rhythm such as times where the user feels tired or anxious. As another illustrative and nonlimiting example, the system is capable of operating at different times during the day such as in the morning prior to user going to work (e.g., prior to a morning meeting), after lunch, etc., to prevent the user from consuming disturbing and/or emotional content.

In one or more other embodiments, the system is also capable of detecting types of digital content that have a positive impact on the user's sleep cycle, e.g., that improve the sleep cycle of the user. In that case, the system is capable of making a suggestion that the user consume such an item of digital content in lieu of one determined to likely have a negative impact on the user's sleep cycle. In particular embodiments, the system is capable of prioritizing digital content determined to have a positive impact on the user's sleep cycle or emotional state over digital content determined to have a negative impact on the user's sleep cycle or emotional state.

The terminology used herein is for the purpose of describing particular embodiments only and is not intended to be limiting. Notwithstanding, several definitions that apply throughout this document now will be presented.

The term "approximately" means nearly correct or exact, close in value or amount but not precise. For example, the term "approximately" may mean that the recited characteristic, parameter, or value is within a predetermined amount of the exact characteristic, parameter, or value.

As defined herein, the terms "at least one," "one or more," and "and/or," are open-ended expressions that are both conjunctive and disjunctive in operation unless explicitly stated otherwise. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without user intervention.

As defined herein, the terms "includes," "including," "comprises," and/or "comprising," specify the presence of stated features, integers, steps, operations, elements, and/or components, but do not preclude the presence or addition of one or more other features, integers, steps, operations, elements, components, and/or groups thereof.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the terms "one embodiment," "an embodiment," "in one or more embodiments," "in particular embodiments," or similar language mean that a particular feature, structure, or characteristic described in connection with the embodiment is included in at least one embodiment described within this disclosure. Thus, appearances of the aforementioned phrases and/or similar language throughout this disclosure may, but do not necessarily, all refer to the same embodiment.

As defined herein, the term "output" means storing in physical memory elements, e.g., devices, writing to display or other peripheral output device, sending or transmitting to another system, exporting, or the like.

As defined herein, the term "processor" means at least one hardware circuit configured to carry out instructions. The instructions may be contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "real time" means a level of processing responsiveness that a user or system senses as sufficiently immediate for a particular process or determination to be made, or that enables the processor to keep up with some external process.

As defined herein, the term "responsive to" means responding or reacting readily to an action or event. Thus, if a second action is performed "responsive to" a first action, there is a causal relationship between an occurrence of the first action and an occurrence of the second action. The term "responsive to" indicates the causal relationship.

The term "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

The terms first, second, etc. may be used herein to describe various elements. These elements should not be limited by these terms, as these terms are only used to distinguish one element from another unless stated otherwise or the context clearly indicates otherwise.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
    analyzing, using computer hardware, digital content before providing the digital content to a device of a user;
    predicting, using the computer hardware, an effect that the digital content will have on a circadian rhythm of the user;
    providing, using the computer hardware, the digital content to the device of the user;
    monitoring a reaction of the user to the digital content;
    determining, by the computer hardware monitoring the reaction of the user to the digital content, that an emotional state of the user is being altered during consumption of the digital content in a manner indicative of a disruption to a sleep cycle of the user; and
    responsive to the determining that the emotional state of the user is being altered during the consumption of the digital content in the manner indicative of the disruption to the sleep cycle of the user, modifying, in real time by the computer hardware, the digital content after delivery of the digital content to the user has started, the modifying the digital content comprising replacing, while the digital content is consumed by the user, at least a first word in a portion of the digital content with at least a second word that is toned down in comparison to the at least the first word.

2. The method of claim 1, wherein the circadian rhythm of the user comprises quality of the sleep cycle of the user.

3. The method of claim 1, wherein the predicting includes comparing the digital content and a time that the digital content is to be presented to the user with historical data for the user that correlates the circadian rhythm of the user with prior consumed digital content and times of delivery of the prior consumed digital content.

4. The method of claim 1, further comprising:
    providing a notification indicating the predicted effect of the digital content on the circadian rhythm of the user.

5. The method of claim 1, wherein the predicting, using the computer hardware, the effect that the digital content will have on the circadian rhythm of the user comprises comparing the digital content with other digital content previously consumed by user that was disruptive to the circadian rhythm of the user.

6. The method of claim 1, wherein the predicting, using the computer hardware, the effect that the digital content will have on the circadian rhythm of the user comprises comparing the digital content with other digital content previously consumed by other users that was disruptive to circadian rhythm of the other users.

7. The method of claim 1, wherein:
the computer hardware is configured to choose from among a plurality of different options for toning down the digital content;
the method further comprising:
detecting that the user is becoming agitated over the digital content as modified by the replacing the at least the first word in the portion of the digital content with the at least the second word that is toned down in comparison to the at least the first word;
responsive to the detecting that the user is becoming agitated over the digital content as modified by the replacing the at least the first word in the portion of the digital content with the at least the second word that is toned down in comparison to the at least the first word:
choosing, by the computer hardware, an increasingly toned down option for toning down the digital content; and
further modifying, in real time by the computer hardware, the digital content after delivery of the digital content to the user has started, the further modifying the digital content comprising replacing, while the digital content is consumed by the user, at least a third word in another portion of the digital content with at least a fourth word that is increasingly toned down in comparison to the at least the second word.

8. A system, comprising:
a processor configured to initiate executable operations including:
analyzing digital content before providing the digital content to a device of a user;
predicting an effect that the digital content will have on a circadian rhythm of the user;
providing the digital content to the device of the user;
monitoring a reaction of the user to the digital content;
determining, by the monitoring the reaction of the user to the digital content, that an emotional state of the user is being altered during consumption of the digital content in a manner indicative of a disruption to a sleep cycle of the user; and
responsive to the determining that the emotional state of the user is being altered during the consumption of the digital content in the manner indicative of the disruption to the sleep cycle of the user, modifying, in real time, the digital content after delivery of the digital content to the user has started, the modifying the digital content comprising replacing, while the digital content is consumed by the user, at least a first word in a portion of the digital content with at least a second word that is toned down in comparison to the at least the first word.

9. The system of claim 8, wherein the circadian rhythm of the user comprises quality of the sleep cycle of the user.

10. The system of claim 8, wherein the predicting includes comparing the digital content and a time that the digital content is to be presented to the user with historical data for the user that correlates the circadian rhythm of the user with prior consumed digital content and times of delivery of the prior consumed digital content.

11. The system of claim 8, wherein the processor is configured to initiate executable operations further comprising:
providing a notification indicating the predicted effect of the digital content on the circadian rhythm of the user.

12. The system of claim 8, wherein the predicting the effect that the digital content will have on the circadian rhythm of the user comprises comparing the digital content with other digital content previously consumed by user that was disruptive to the circadian rhythm of the user.

13. The system of claim 8, wherein the predicting the effect that the digital content will have on the circadian rhythm of the user comprises comparing the digital content with other digital content previously consumed by other users that was disruptive to circadian rhythm of the other users.

14. The system of claim 8, wherein:
the system is configured to choose from among a plurality of different options for toning down the digital content;
the executable operations further comprising:
detecting that the user is becoming agitated over the digital content as modified by the replacing the at least the first word in the portion of the digital content with the at least the second word that is toned down in comparison to the at least the first word;
responsive to the detecting that the user is becoming agitated over the digital content as modified by the replacing the at least the first word in the portion of the digital content with the at least the second word that is toned down in comparison to the at least the first word:
choosing an increasingly toned down option for toning down the digital content; and
further modifying, in real time, the digital content after delivery of the digital content to the user has started, the further modifying the digital content comprising replacing, while the digital content is consumed by the user, at least a third word in another portion of the digital content with at least a fourth word that is increasingly toned down in comparison to the at least the second word.

15. A computer program product comprising a computer readable storage medium having program instructions embodied therewith, the program instructions executable by a processor to cause the processor to initiate executable operations comprising:
analyzing digital content before providing the digital content to a device of a user;
predicting an effect that the digital content will have on a circadian rhythm of the user;
providing the digital content to the device of the user;
monitoring a reaction of the user to the digital content;
determining, by the monitoring the reaction of the user to the digital content, that an emotional state of the user is being altered during consumption of the digital content in a manner indicative of a disruption to a sleep cycle of the user; and
responsive to the determining that the emotional state of the user is being altered during the consumption of the digital content in the manner indicative of the disruption to the sleep cycle of the user, modifying, in real time, the digital content after delivery of the digital content to the user has started, the modifying the digital content comprising replacing, while the digital content is consumed by the user, at least a first word in a portion of the digital content with at least a second word that is toned down in comparison to the at least the first word.

16. The computer program product of claim 15, wherein the circadian rhythm of the user comprises quality of the sleep cycle of the user.

17. The computer program product of claim 15, wherein the predicting includes comparing the digital content and a time that the digital content is to be presented to the user with historical data for the user that correlates the circadian rhythm of the user with prior consumed digital content and times of delivery of the prior consumed digital content.

18. The computer program product of claim 15, wherein the predicting the effect that the digital content will have on the circadian rhythm of the user comprises comparing the digital content with other digital content previously consumed by user that was disruptive to the circadian rhythm of the user.

19. The computer program product of claim 15, wherein the predicting the effect that the digital content will have on the circadian rhythm of the user comprises comparing the digital content with other digital content previously consumed by other users that was disruptive to circadian rhythm of the other users.

20. The computer program product of claim 15, wherein:
the processor is configured to choose from among a plurality of different options for toning down the digital content;
the executable operations further comprising:
detecting that the user is becoming agitated over the digital content as modified by the replacing the at least the first word in the portion of the digital content with the at least the second word that is toned down in comparison to the at least the first word;
responsive to the detecting that the user is becoming agitated over the digital content as modified by the replacing the at least the first word in the portion of the digital content with the at least the second word that is toned down in comparison to the at least the first word:
choosing an increasingly toned down option for toning down the digital content; and
further modifying, in real time, the digital content after delivery of the digital content to the user has started, the further modifying the digital content comprising replacing, while the digital content is consumed by the user, at least a third word in another portion of the digital content with at least a fourth word that is increasingly toned down in comparison to the at least the second word.

\* \* \* \* \*